United States Patent [19]

Winans, Jr. et al.

[11] Patent Number: 4,983,163

[45] Date of Patent: Jan. 8, 1991

[54] METHOD, COMPOSITIONS AND ARTICLES FOR PREVENTION AND TREATMENT OF HERPES SIMPLEX VIRUS INFECTIONS

[75] Inventors: Luther Winans, Jr.; Terry L. Foster, both of Abilene, Tex.

[73] Assignee: Science Research Center, Inc., Abilene, Tex.

[21] Appl. No.: 589,158

[22] Filed: Mar. 13, 1984

Related U.S. Application Data

[63] Continuation-in-part of Ser. No. 309,936, Oct. 9, 1981, abandoned.

[51] Int. Cl.$^5$ .............................................. A61M 31/00
[52] U.S. Cl. ........................................ 604/49; 604/904

[58] Field of Search ............... 128/157, 260, 261, 210; 435/174, 179, 853, 854; 424/27, 28, 93; 604/55, 892, 896, 285–288, 354, 904, 49

[56] References Cited

U.S. PATENT DOCUMENTS

| 2,579,403 | 12/1951 | Slomowitz | 604/286 |
| 3,567,821 | 3/1971 | Nouvel | 424/93 |
| 3,639,566 | 2/1972 | Naito et al. | 424/37 |

*Primary Examiner*—Ferris H. Lander

[57] ABSTRACT

Methods, compositions and articles are disclosed which are useful in the treatment of humans suffering from herpes simplex virus infections. In an embodiment method, herpes simplex type 2 virus infecting the genital tract of a female is treated by administering a viable, mixed culture of *L. acidophilus* and *L. bulgaricus* on a catamenial tampon.

4 Claims, 2 Drawing Sheets

METHOD, COMPOSITIONS AND ARTICLES FOR PREVENTION AND TREATMENT OF HERPES SIMPLEX VIRUS INFECTIONS

CROSS-REFERENCE TO RELATED APPLICATION

This application is a continuation-in-part of copending U.S. patent application Ser. No. 309,936 filed Oct. 9, 1981, now abandoned.

BACKGROUND OF THE INVENTION

1. Field of the Invention

The invention relates to methods, compositions and articles useful in the prophylaxis and treatment of active viral infections and more particularly relates to the treatment of herpes simplex virus infections in humans.

2. Brief Description of the Prior Art

In recent months, public attention has been focused on the major increase in the number of infections reported in humans and attributed to the herpes simplex virus, particularly the type 2 virus. The type 2 virus is generally associated with genital infections, i.e., herpes infections such as Herpes genitalis and Herpes labialis. Such infections are not limited however to infections of the genitals, but also include Dermatitis and Gingivostomatitis herpetica, Encephalitis herpetica, Herpes zoster and Varicella. The type 1 herpes simplex virus is also prevalently hosted in humans and is more often associated with symptomatic lesions in or near the oral zones.

Infections in humans, due to the herpes simplex virus of types 1 and 2 have been highly resistant to treatment. There has been no known prophylactic treatment. The present invention comprises a method as well as compositions and articles which are useful in prophylaxis and treatment of the active state of the infections. The "active" state of the infection is defined herein as the phase during which symptomatic lesions, i.e.; sores, blisters, ulcers, etc., appear in affected areas such as around the mouth (type 1 virus) or in the genital areas (type 2 virus). This is in contrast to the "hidden" or remissive state wherein symptoms of the infection are not observed.

Toxic shock syndrome is an often fatal entity, believed to be precipitated by the presence of an enterotoxin produced by the microorganism *Staphylococcus aureus*. Occurrence of the syndrome in female humans appears to be associated with the use of catamenial tampons although the relationship is not fully understood. In any event, we believe that the toxin is removed or at least its effect neutralized by the presence of a viable colony of the microorganisms *Lactobacillus acidophilus* and/or *Lactobacillus bulgaricus*. Certain embodiment articles of our invention are particularly useful therefore in eliminating toxic shock syndrome as a hazard associated with catamenial tampons.

SUMMARY OF THE INVENTION

The invention comprises a method of alleviating the suffering of a mammal suffering from the infection of a herpes simplex virus, which comprises; administering to the mammal an anti-herpetically effective amount to relieve said suffering of a viable culture selected from the group consisting of *Lactobacillus acidophilus*, *Lactobacillus bulgaricus* and mixtures thereof or their metabolic products.

The invention further comprises compositions of viable cultures as described above in admixture with pharmaceutical carriers which adapt the cultures to their use in the method of the invention.

The invention also comprises an applicator pad containing vacuum-dried, viable, cultures of *Lactobacillus acidophilus*, *Lactobacillus bulgaricus* and mixtures thereof.

The applicator pads are useful in the treatment and prophylaxis of active herpes simplex virus infections. Applicator pads which are catamenial tampons may also be useful as a preventive of toxic shock syndrome. These uses of the pads of the invention also comprise our invention.

DETAILED DESCRIPTION OF THE PREFERRED EMBODIMENTS OF THE INVENTION

The microorganisms *Lactobacillus acidophilus* and *Lactobacillus bulgaricus* are well known as are conditions certain embodiment method and articles of the invention, cultures of these microorganisms (preferably mixtures of cultures of both microorganisms) are dispersed on or within applicator pads and dried (preferably freeze-dried) in-situ. The methods and techniques of heat and vacuum drying and freeze-drying (lyophilizing) microorganism cultures are well known and need not be described in detail herein.

The dried cultures of the *L.acidophilus* and/or *L. bulgaricus* remain viable and when moistened under growing conditions will resume activity and growth on the applicator pads or on suitable environmental substrate surfaces which are inoculated by contact with the applicator pad.

Figure 1:
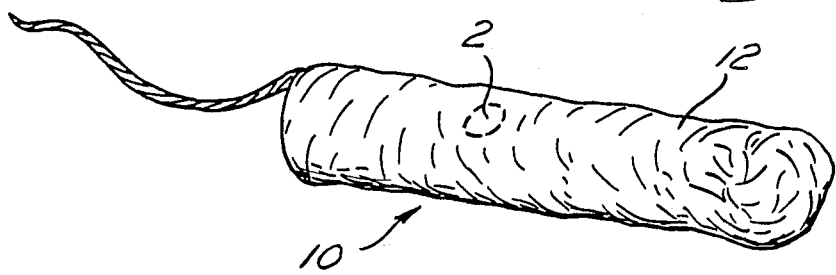
FIG. 1 is a view-in-perspective of an embodiment pad of the invention.
Figure 2:
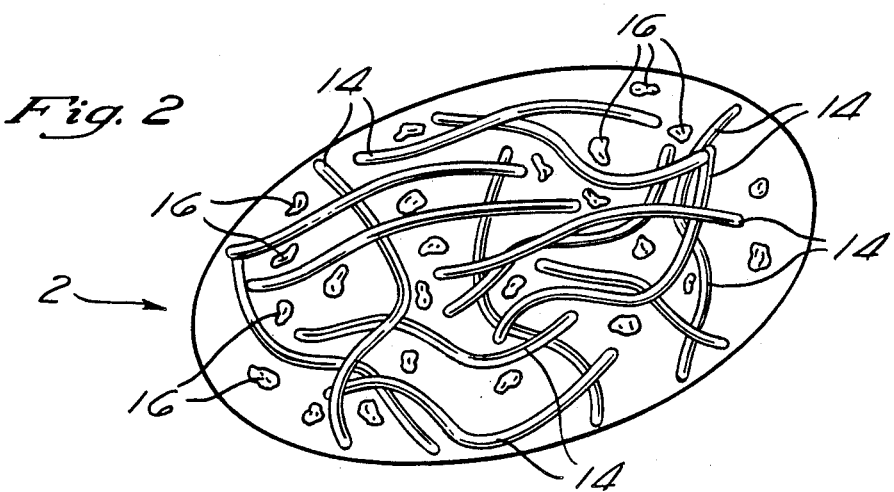
FIG. 2 is an enlarged view of a portion of the pad shown in FIG. 1.

Applicator pads employed as components of the articles of the invention may be any conventional type of absorbent pad, preferably one which will absorb and hold moisture. Generally preferred are absorbent pads of textile materials such as natural or synthetic absorbent fibers. In FIG. 1 of the accompanying drawings, a preferred applicator pad for use in the treatment of female humans suffering from active herpes simplex type 2 virus is shown. The catamenial tampon 10 is a conventional catamenial tampon made of an absorbent body 12 of cotton fibers 14. FIG. 2 is an enlarged view of the zone 2 shown in FIG. 1 and shows that the fibers 14 of the tampon 10 form a matrix to hold dried particles 16 in place. The tampon 10, contains the dried particles 16, which are preferably freeze-dried particles of a culture of *L. acidophilus* and/or *L. bulgaricus*, in a viable condition for useful periods of time when packaged in a hermetically sealed container under normal storage conditions (at room temperature, moisture free and protected from light).

When desired for use in the treatment of a female human suffering from genital herpes, i.e.; a herpes simplex type 2 infection, the tampon 10 may be inserted into the vaginal canal where it will be moistened by vaginal fluids. This moisture will activate the freeze-dried particles 16 to grow. Colonization invariably occurs on the contacted mucous membrane of the vagina itself. This is advantageous since the lactobaccili have often been observed as normal vaginal flora in healthy individuals. The tampon 10 as a catamenial device may be used in the conventional manner, being removed and replaced one or more times daily until the desired result is obtained, i.e.; relief of suffering.

When the lactobacilli establish on the mucous membrane of the herpes simplex virus infected individual, it will be observed that mucocutaneous lesions (ulcers or vesicles) which are symptomatic of the active phase of the viral infection diminish. The growing lactobacilli apparently inhibit the virus. Although we are not to be bound by any theory of operation, presence of the growing flora may in some way interfere with replication of the virus. In any event, the symptomatic lesions (which can be painful and cause suffering to the infected individual) are apparently healed and suffering alleviated. The active phase of the infection is inhibited and this is of advantage in preventing transmission of the infection to other individuals who contact the infected areas of the female.

Figure 3:
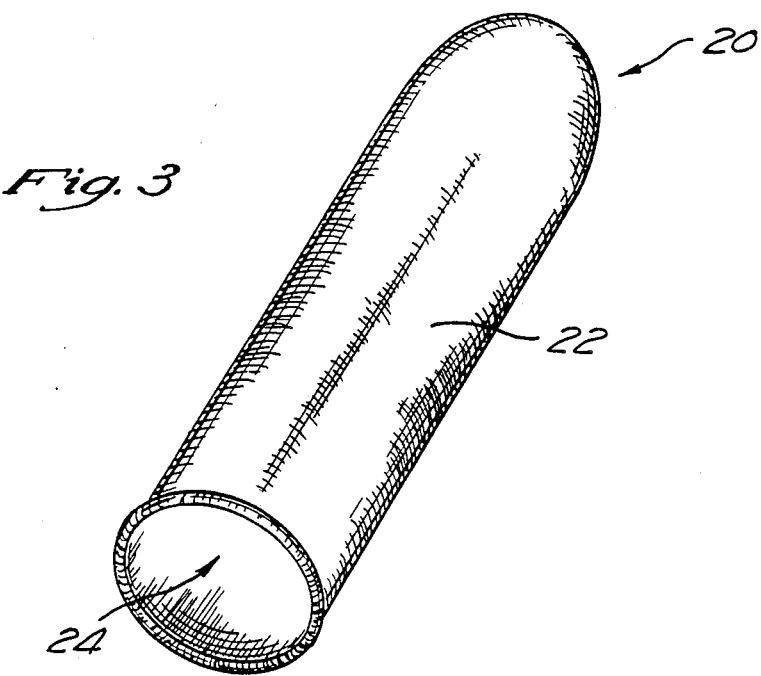
FIG. 3 is a view-in-perspective of another embodiment pad of the invention.

As a method of treating active infections of herpes simplex virus type 2, the method of the invention is not limited to treatment of female humans. When active lesions appear in the genital areas of a male human, the applicator pads may be fabricated to bandage those areas including the penis. FIG. 3 is a view-in-perspective of a bandage type applicator pad 20 in the form of a penis sheath. The body 22 may be, for example, a stretchable, knitted fabric of moisture absorbent textile into which the dried culture of L. acidophilus and/or L. bulgaricus may be incorporated as in tampon 10. When a herpes simplex type 2 virus infected male human shows or exhibits active penile lesions, the sheath 20 may be slipped on the penis through opening 24 and the sheath 20 moistened with water to activate or revive the microorganism culture. The effect on the active virus site will be similar to that observed in the female, except of course new flora of the microorganism are not likely to establish on the epidermis of the patient. However, the herpes lesions will heal more rapidly than otherwise, alleviating suffering of the infected male.

The following examples describe the manner and process of making and using the invention and set forth the best mode contemplated by the inventors for carrying out the invention but are not to be construed as limiting.

EXAMPLE 1

A. Lactobacillus Cultures

*Lactobacillus acidophilus* and *lactobacillus bulgaricus* are each grown separately by inoculating each into micro inoculum broth by adding 1 ml of a 48 hr culture to 100 ml of broth. The cultures are then placed in an incubator containing 5% carbon dioxide in air and incubated for 42-72 hours at a temperature of 38° C. The lactobacillus cultures are then titered and adjusted to a viable cellular concentration of approximately $2.0 \times 10^8$ cells per ml using sterile phosphate buffered saline (PBS).

B. Inoculation of Tampons

Commercially available catamenial tampons with plastic applicators (inserters) are aseptically opened and placed in a sterile holder. The lactobacillus cultures are stirred and equal volumes of *L. acidophilus* and *L. bulgaricus* mixed together. To each tampon, 5 ml of the mixed lactobacillus suspension is aseptically added at the base (plunger end or string end) and the suspension allowed to soak into the tampon material under laminar flow.

C. Drying of Tampons

After the mixed lactobacillus suspension has been absorbed into the tampon material the tampons are placed on a sterile stainless steel holder. Sterile foil is then placed loosely over the top end of the tampons and the tampons are then placed in a vacuum freeze-dryer (lyophilizer) for 24 or 48 hours. The tampons are then removed from the lyophilizer and sealed within the sterile foil.

Representative tampons are subsequently moistened and assayed for viability of the cultures. The drying time and the counts observed are shown in the Table 1, below.

TABLE 1

| LACTOBACILLUS - TAMPON COUNTS | | | |
|---|---|---|---|
| | COUNTS $10^8$ CFU PER ML) | | DRYING |
| SAMPLE NO. | INOCULUM | TAMPONS | TIME |
| A-1 | 2.67 | 0.88 | 24 Hrs. |
| A-2 | 2.58 | 0.95 | 24 Hrs. |
| A-3 | 2.73 | 0.90 | 24 Hrs. |
| A-4 | 2.71 | 0.80 | 24 Hrs. |
| A-5 | 2.62 | 0.79 | 24 Hrs. |
| Average | (2.66) | (0.86) | 24 Hrs. |
| B-1 | 2.43 | 0.74 | 48 Hrs. |
| B-2 | 2.65 | 0.77 | 48 Hrs. |
| B-3 | 2.54 | 0.50 | 48 Hrs. |
| B-4 | 2.58 | 0.69 | 48 Hrs. |
| B-5 | 2.51 | 0.79 | 48 Hrs. |
| Average | (2.54) | (0.70) | 48 Hrs. |

The tampons may be used in the manner conventional to the use of a catamenial tampon without fear of inducing or contributing to toxic shock syndrome. In addition, when inserted in the vaginal canal of a female human suffering from herpes simplex virus type 2, colonies of the mixed lactobacilli will generally establish itself as part of the flora of the mucosa lining the canal. Presence of the lactobacilli inhibits and suppresses the active phase in an infected female, alleviating suffering associated with the herpes simplex virus type 2 infection.

EXAMPLE 2

*Lactobacillus acidophilus* and *Lactobacillus bulgaricus* cultures are provided following the procedure of Example 1, Part A, supra, and equal volumes of each culture are mixed together.

Separately, a culture of herpes simplex type 2 virus is provided.

A series of tissue cultures are prepared using human embryonic epithelial cells. A portion of the cell cultures are inoculated with $10^8$ cells each of the lactobacillus preparation described above and incubated at 37° C. for 1 hour. The cultures are then infected with active virus from the virus culture. As a control, a portion of the tissue cell cultures are not inoculated with the lactobacillus preparation prior to exposure to the virus. Also, in a separate series, 95 IU/ml of penicillin and 95 mcg/ml. of streptomycin are added to the cell cultures as controls.

After a period of incubation, each of the series of tissue cultures and controls are then examined (incubation at a temperature of 37° C. for 24 hours, and 48 hours) for cytophathic effect on the tissue cells. Cells characterized by abnormal rounding, cytoplasmic bridging, granulation and cell lysis were counted as having been affected by the virus presence. The results are shown in Table 2, below.

TABLE 2

| ASSAY SAMPLE (TREATMENT) | CYTOPATHIC EFFECT | |
|---|---|---|
|  | 24 Hr % CPE | 48 Hr % CPE |
| Virus + Lac. Prep. | 0 | 0 |
| Virus + Lac. Prep. + P.S* | 5 | 15 |
| CONTROLS |  |  |
| Virus Only | 75 | 95 |
| Lac. Prep. Only | 2 | 2 |
| Virus + P.S* | 80 | 97 |
| Lac. Prep. + P.S* | 0 | 0 |
| Cells Only: Untreated | 0 | 0 |
| Cells Only: Untreated + P.S* | 0 | 0 |

*Penicillin and Streptomycin added.

From the Table 2, supra., it will be observed that presence of the lactobacillus preparation apparently protects the cells from damage attributed to the virus. The mechanism of the protection, i.e.; viricidal activity or interference of virus replication is not presently known.

Those skilled in the art will appreciate that many modifications may be made to the above-described preferred embodiments of the invention without departing from the spirit and the scope of the invention. For example, applicator pads of the invention may be made from a wide variety of materials, including polymeric resin foams and the like, in a wide variety of useful shapes and sizes for intra-oral as well as intravaginal use and for topical administration of the Lactobacillus. Also, the applicator pads of the invention may be used to treat lesions of the type 1 virus in infected individuals.

EXAMPLE 3

One hundred five female BALP/c mice were obtained from Timco Breeding Laboratories (Houston, Tex.). Each animal was 3-4 weeks old and weighed between 18-20 grams. Each animal was examined then placed ten to a cage and held in quarantine for 14 days.

Penicillin and streptomycin were obtained from KC Biological Company as an aqueous solution containing 10,000 units/ml of penicillin and 10,000 mcg/ml of streptomycin. Amphotericin-B (Fungizone) was obtained from Flow Laboratories, Inc. as a 250 mcg/ml solution. Gentamicin was obtained from Schering Corporation as a 50 mg/ml solution.

Trypsin, 1:250, was obtained from KC Biological Company as a 10X concentrate. It was prepared as a 0.25% solution by the addition of phosphate buffered saline. The solution was stored at 4° C. then equilibrated to 36° C. prior to use.

Trypan blue was obtained from Flow Laboratories, Inc. and stored in the dark at room temperature until needed.

The phosphate buffered saline (PBS) was prepared by adding 8 grams of sodium chloride, 0.2 grams of potassium chloride, 1.15 grams of disodium hydrogen phosphate and 0.2 grams of potassium chloride, 1.15 grams of disodium hydrogen phosphate and 0.2 grams of potassium dihydrogen to one liter of distilled water. The solution was sterilized by autoclaving at 121° C. for 20 minutes then allowed to cool to room temperature. To five milliliters of distilled water, 0.1 gram of calcium chloride and 0.1 gram of magnesium chloride was added and allowed to stir until dissolved. The solution was sterilized by filtration through a 0.22 um membrane filter. The two salt solutions were then mixed together and stored at 4° C. To the PBS used to resuspend the virus, fetal bovine serum was added to give a concentration of 0.5%.

Iodonitrotetrazolium violet (2-(p-iodophenyl)-3-(p-nitrophenyl)-5-phenyl tetrazolium chloride) was obtained from Sigma Chemical Company and prepared as a 90 mg/ml solution containing 1% Noble agar (Difco). The solution was sterilized by autoclaving at 121° C. for 15 minutes and then stored at 4° C. The solution was melted in boiling water and equilibrated to 44° C. prior to its use.

A continuous cell line established from human embryonic lung (MRC-V) was used in this example. The cells were obtained from Flow Laboratories, Inc. The cells were passed upon receipt, frozen and stored in liquid nitrogen at a cell density of $4.7 \times 10e6 \times 10e6$ cell/ml.

The cells were removed from the storage canister and quickly thawed in a 37° C. water bath. The outside of the ampule was washed with sterile 70% isopropyl alcohol. The ampule was opened and the contents transferred to a 25 cm" tissue culture flask containing 5 ml of growth medium (EMEM). The cells were dispersed by aspirating several times through a 5 ml pipette (triturate). An additional 5 ml of growth medium was added. The flask was gently rocked then placed into a 36° C. incubator with 5% carbon dioxide.

After the cells had formed a confluent monolayer (7-10 days), the cultures were split. Confluent monolayers were washed by adding 5 ml of phosphate buffered saline (PBS) without the calcium or magnesium salts. The PBS was decanted and the monolayer trypsinized by adding 2 ml of a 0.25% trypsin solution and allowing culture to sit for 30 seconds. The trypsin solution was decanted and allowed to stand at room temperature for 60-70 seconds. Five milliliters of growth medium was added to each culture and the cells suspended by triturating several times with a 5 ml pipette. The cell suspension was split by transferring 2.5 ml to a 25 cm" flask containing 5 ml of growth medium. The suspension was gently rocked then placed into a 36° C. incubator with 5% carbon dioxide. The cultures were incubated until confluent then used in culturing the virus.

The cells were enumerated using an AO Spencer, hemocytometer counting chamber. Viability was determined by adding 0.5 ml of 0.5% trypan blue to 1 ml of cell suspension. The trypan blue was selectively adsorbed by the non-viable cells which stain an intense blue while the viable cells remain unstained.

Herpes simplex virus type 2, strain G was obtained from the American Type Culture Collection. The culture was received in lyophilized form. The titer was marked as 10e5 TCID/0.2 ml in 12 days. The culture was opened and passed in MRC-V cell culture and then frozen and stored in liquid nitrogen.

The virus suspension was removed from cold storage and quickly thawed by placing into a 36° C. water bath. The outside of the ampule was washed with sterile 70% isopropyl alcohol, opened and 1 ml of sterile PBS added. The suspension was aspirated several times then 0.5 ml transferred to each of two confluent cell cultures after decanting the growth medium. The culture was gently rocked to dispense the virus inoculum and then placed at 35° C. for 60 minutes. The culture was rocked every 10–15 minutes to prevent the monolayer from drying. The culture was removed from the incubator and 5 ml of growth media added and returned to the 35° C. incubator with 5% carbon dioxide. The culture was examined at 24 and 48 hours for any cytopathic effect (CPE). The CPE was characterized by giant cell formation, cytoplasmic bridging, and cell lysis. The culture was removed from the incubator and the medium collected and stored in a sterile screw top tube at −75° C. Five milliliters of growth medium was added to the culture and then returned to the incubator. After an additional 24–30 hours, the culture was again examined. The culture was allowed to progress to the 4+ stage (75–100% of the cells affected). The infected cell culture was placed into a −5° C. freezer and allowed to freeze. The culture was removed from the freezer and allowed to thaw. This freeze-thaw cycle procedure was repeated twice more for a total of three cycles. The cell-virus suspension was mixed with the thawed 24 hour suspension then transferred to sterile conical, 50 ml centrifuge tubes. The tubes were capped and centrifuged at 2500 rpm (425×g) for 10 minutes at 4° C. The supernatant was removed and saved. The virus suspension (supernatant) was used to inoculate additional cell cultures.

The final virus suspension was prepared by collecting the virus-cell suspension, centrifuging at 2500 rpm, and transferring the supernatant to sterile centrifuge tubes. The suspension was centrifuged at 35,000 rpm (75,000×g) for three hours. Approximately 90% of the supernatant was removed and phosphate buffered saline containing 0.5% fetal bovine serum was added to give one third of the original volume. The suspension was stored at 4° C.

A tenfold serial dilution series was prepared by adding 0.2 ml of the virus suspension to 1.8 ml of growth medium. The suspension was mixed and 0.2 ml transferred to another 1.8 ml media blank. This procedure was carried out multiple times to produce a 1:10 to 1:10,000,000 dilution series. As each dilution was prepared, 0.2 ml of the preceding dilution was plated on each of two confluent monolayers in 60 mm plates from which the culture medium had been removed. The inoculated cultures were placed into a 35° C. incubator with 5% carbon dioxide for one hour. The cultures were rocked every 10–15 minutes to prevent drying. Three milliliters of nutrient agar overlay medium was added to each infected cell culture and left at room temperature to solidify. Each culture was inverted and placed into the 35° C. incubator with 5% carbon dioxide. After 72 hours, 2 ml of melted staining agar (iodonitrotetrazolium chloride) was added to each culture. The cultures were kept at room temperature until the agar overlay solidified then returned to the incubator for 24 hours. Cultures showing distinct plaque morphology were counted and averaged to obtain the final number of plaque forming units (pfu) in the virus suspension.

The lactobacillus cultures were obtained from Hynson, Westcott & Dunning as pure cultures of *Lactobacillus acidophilus* and *Lactobacillus bulgaricus* in evaporated milk. The cultures were subcultured and grown in evaporated milk then lyophilized and stored at −75° C.

The lyophilized cultures were removed from cold storage and 1 ml of micro inoculum broth added to each. The *L. acidophilus* suspension was inoculated into 300 ml of micro inoculum broth containing 0.52% thiotone peptone. The *L. bulgaricus* was inoculated into 300 ml of micro inoculum broth that was pre-incubated for three hours prior to use. Both cultures were placed into a 38° C. incubator with 5% carbon dioxide.

The cultures were removed from the incubator and examined for purity by gram staining and subculturing. The pH of each culture was adjusted to 7.0 using sterile 1N NaOH. Each culture was titered using a tenfold serial dilution series and micro inoculum agar pour plates. The cultures were stored at 4° C. for 48 hours until the results of the titer were obtained. The cultures were adjusted (by the addition of sterile PBS or centrifugation and removal of medium) to contain approximately $2 \times 10e7$ cells per milliliter. Both cultures (*L.acidophilus* and *L.bulgaricus*) were mixed together in equal parts (1:1). The pH of the mixed culture suspension was measured and adjusted to 7 if necessary. The mixture was titered using a tenfold serial dilution series. The mixture was stored at 4° C. until needed.

Media used for cell culturing was Minimum Essential Medium Eagle, Earle's salts (EMEM) with L-glutamine and phenol red, without sodium bicarbonate. The medium was obtained from KC Biological (Catalog # IM-305). The contents of one vial was dissolved in 800 ml of distilled water. To this solution 2.2 grams of sodium bicarbonate was added. Additional water was added to bring the final volume to 1 liter. The pH was tested and adjusted, if necessary, to 7.1–7.2. The medium was sterilized using positive pressure filtration. The solution was filtered through a Millipore Sterivex-GS type 0.22 um membrane filter (Catalog # SVGS01015). Five milliliters of the penicillin-streptomycin solution, 4 ml of the Amphotericin-B and 1 ml of Gentamicin was added to 500 ml of media (EMEM). This yields a final concentration of approximately 90 units/ml of penicillin, 90 mcg/ml of streptomycin, 1.8 mcg/ml Amphotercin-B and 90 mcg/ml Gentamicin.

Fetal bovine serum (FBS) was obtained from KC Biological Company. The FBS was mycoplasma-tested and virus screened. The serum was stored at −75° C. and thawed prior to use. The growth medium was prepared by adding 65 ml of FBS to the 510 ml of EMEM-antibiotic medium. The final serum concentration was approximately 10–11 percent.

Noble agar was obtained from Difto Laboratories and prepared as a 2% (w/v) solution. This was sterilized by autoclaving at 121° C. for 15 minutes then stored at room temperature. The nutrient agar for overlaying virus cultures was prepared by melting 50 ml of 2% noble agar and mixing with 44 ml of double strength EMEM and 6 ml of FBS. These solutions were equilibrated to 44° C. before mixing and prior to use.

Micro Inoculum broth was obtained from Difco Laboratories as a dehydrated powder (Catalog # 0320-01). The medium was prepared by dissolving 11.1 grams of the powdered base in 300 ml of distilled water. To the medium used to grow the *L. acidophilus*, 1.5 grams of thiotone peptone was added. The medium was sterilized by autoclaving at 118° C. for 25 minutes. The medium to be inoculated with the *L. bulgaricus* was preincubated for 3 hours prior to inoculation. Lactobacillus plate counts were run using the micro inoculum broth with 1.5% granulated agar added. The counts were prepared as tenfold serial dilutions and plated using the pour plate method.

The double strength minimum essential medium was prepared using Hank's balanced salt (HBS) 10×w/o phenol red (KC Biological # LM-223-1). To 200 ml of distilled water, 100 ml of HBS, 10 ml of 100×MEM amino acid solution (Catalog # LM-174-1), 10 ml of 100×MEM vitamine solution (Catalog # LM-172-1), 10 ml of 100×L-glutamine (Catalog # LM-233-2) and 1 gram of glucose was added. The solution was allowed to stir then 5 ml of the penicillin-streptomycin solution, 1 ml of the gentamycin sulfate solution, 4 ml of the Amphotericin-B, and 0.4 grams of sodium bicarbonate was added. Additional water was added to bring the volume to 500 ml. The pH was tested and adjusted to 7.0-7.2 using 1N NaOH. The solution was stored at 4° C.

Experimental Groups

The mice were set-up into five groups. A positive control group (Group A) of 40 animals, two treatment groups of twenty animals each (Group B & C), a negative control group of fifteen animals (Group D) and a treatment only control group of 10 animals (Group E).

Forty mice were used as positive controls. This group (Group A) received the virus inoculum without the lactobacillus treatment. The animals were divided into four subgroups. One group of ten mice received the viral inoculum for three days followed by three days of phosphate buffered saline with 0.5% FBS (VIRUS-PBS). The second subgroup of ten mice received PBS-FBS for three days followed by viral inoculation for three days.(PBS-VIRUS). The third group of ten mice received the virus inoculation for three days followed by three days of micro inoculum broth (VIRUS-MICRO). The last subgroup received the micro inoculum broth for three days followed by three days of virus inoculum (MICRO-VIRUS).

Two groups of twenty mice each were set-up to test the antiviral activity of the lactobacillus preparation. One lactobacillus for three days followed by three days of the viral inoculum (LAC-VIRUS). The second group of twenty mice (Group C) were post-treated. In this group each animal received the viral inoculum for three days followed by three days of lactobacilli inoculation (VIRUS-LAC). The animals were kept in cages of ten mice each.

Two additional control groups were set-up. One group of fifteen mice (Group D) were used as a negative control. The animals in this group received no virus and no lactobacilli. The animals were divided into three subgroups of five mice each. One subgroup received PBS-FBS only for six days (PBS-PBS). Another subgroup received micro inoculum broth for three days followed by PBS-FBS for three days (MICRO-PBS). The third subgroup received no inoculation of any kind (NO INOC). The second control group (Group E) consisted of ten mice and was used as a treatment control. These animals were not inoculated with the virus but received only the lactobacilli. This group was subdivided into two subgroups of five mice each. One subgroup receiving the lactobacillus inoculation for the first three days followed by PBS-FBS for the next three days (LAC-PBS). The second subgroup received the PBS-FBS for three days then the lactobacilli for three days (PBS-LAC).

Each animal scheduled for inoculation received 50 ul of inoculum daily for six days. The inoculations were given in two sets of three days each. Each inoculum was given by vaginal route using a micro pipette. The 50 ul inoculum was slightly in excess to allow for the exposure of the external vulva during inoculation. After the introduction of the sample, sterile cotton "tampons" (small dental filling material) were inserted.

The animals were observed for 37 days. The date and time an animal was found dead was recorded and each examined for lesions or other gross abnormalities. All animals were examined daily for the appearance of external lesions or other abnormalities. When possible, each dead animal was examined internally for any internal abnormalities especially of the lungs and abdominal cavity. The total number of deaths in each group was recorded and logged twice daily for the first five days, then four times daily for the next twenty-two days and twice daily again for the next ten days.

The titer of the virus suspension at the start of the inoculation period was $2.7 \times 10e5$ pfu/ml. Each animal inoculated with the virus received approximately $1.35 \times 10e4$ plaque forming units for the first three days. The virus titer at the start of the next three day period was $1.5 \times 10e5$ pfu/ml. The inoculum during this time contained about $7.5 \times 10e3$ pfu. The virus suspension at the end of the six day inoculation period was $1.44 \times 10e5$ pfu/ml.

The titer of the lactobacillus mixture at the start of the inoculation period was $1.81 \times 10e7$ cfu/ml or $9.05 \times 10e5$ cfu per inoculum. The lactobacillus titer at the third day was $1.19 \times 10e7$ cfu/ml. The inoculum contained approximately $5.95 \times 10e5$ cfu. The lactobacillus count on the last day of the inoculation series was $1.13 \times 10e7$ cfu/ml.

The results for the assay are presented in Table 3, below.

TABLE 3
THE EFFECT OF LACTOBACILLI TREATMENT ON HERPES SIMPLEX VIRUS TYPE 2 IN BALP/c MICE

| (GROUP) | TREATMENT | TOTAL ANIMALS | ANIMALS SURVIVING NO. | % | ANIMALS DYING NO. | % |
|---|---|---|---|---|---|---|
| (A) | POSITIVE CONTROL: | | | | | |
| | VIRUS-PBS | 10 | 2 | 20 | 8 | 80 |
| | VIRUS-MICRO | 10 | 1 | 10 | 9 | 90 |
| | PBS-VIRUS | 10 | 2 | 20 | 8 | 80 |
| | MICRO-VIRUS | 10 | 1 | 10 | 9 | 90 |
| | TOTAL | 40 | 6 | 15 | 34 | 85 |
| (B) | POST-TREATMENT: | | | | | |
| | VIRUS-LAC | 10 | 5 | 50 | 5 | 50 |
| | VIRUS-LAC | 10 | 6 | 60 | 4 | 45 |
| | TOTAL | 20 | 11 | 55 | 9 | 45 |
| (C) | PRE-TREATMENT | | | | | |
| | LAC-VIRUS | 10 | 8 | 80 | 2 | 20 |
| | LAC-VIRUS | 10 | 9 | 90 | 1 | 10 |
| | TOTAL | 20 | 17 | 85 | 3 | 15 |
| (D) | NEGATIVE CONTROL: | | | | | |
| | MICRO-PBS | 5 | 4 | 80 | 1 | 20 |
| | PBS-PBS | 5 | 5 | 100 | 0 | 0 |
| | NO INOC | 5 | 5 | 100 | 0 | 0 |
| | TOTAL | 15 | 14 | 93 | 1 | 7 |
| (E) | TREATMENT CONTROL: | | | | | |
| | LAC-PBS | 5 | 5 | 100 | 0 | 0 |
| | PBS-LAC | 5 | 5 | | 0 | 0 |
| | TOTAL | 10 | 10 | 100 | 0 | 0 |

From Table 3, supra., it will be observed that those animals receiving only the virus inoculation had a mortality rate of 80 to 90% (Group A). The mice receiving the virus and the micro inoculum broth (subgroups 2 & 4) had the highest mortality with 9 of 10 dying. In the virus/PBS groups (subgroups 1 and 3) 8 of 10 mice died (80% mortality). Six mice survived out of a total of 40 mice in this group. This gives a 15% survival rate (85% mortality) of all those animals receiving the virus with no lactobacillus treatment. The mice inoculated with the virus and the micro inoculum broth had a 10% higher mortality than those receiving the virus and the phosphate buffered saline.

Figure 4:
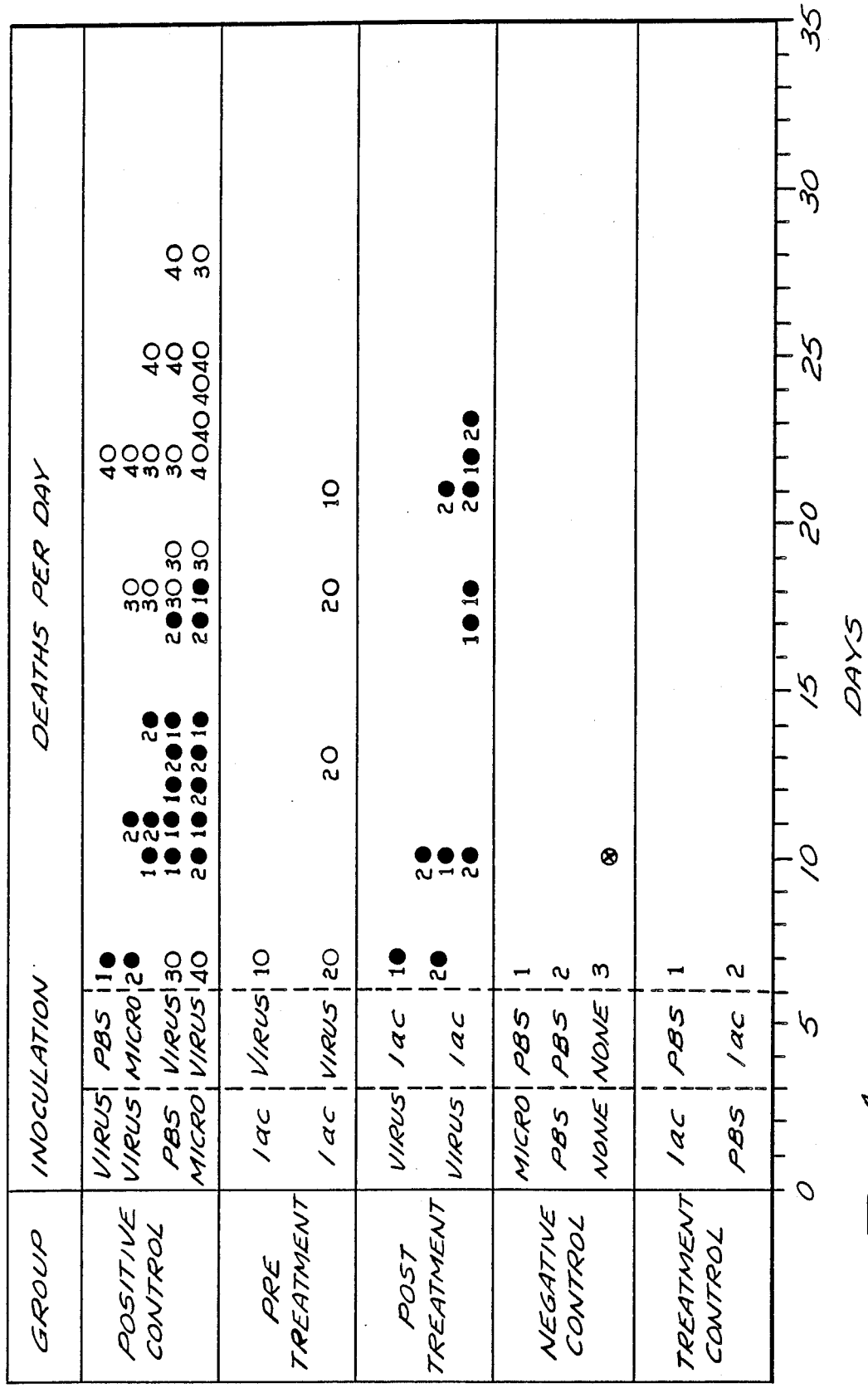
FIG. 4 graphically portrays the results of Example 3, herein.

As shown in FIG. 4 of the accompanying drawings, the first deaths occurred 10 days after the start of virus inoculation. In subgroups 1 and 2 the virus was inoculated first followed by the PBS or the micro inoculum broth. The first deaths occurred in these groups. The distribution of the deaths in these groups appeared relatively equal. Thirteen of the twenty animals (65%) died in a five day period from day 10 to day 14. Three additional deaths occurred at day 17 and 18 for a total of 17 deaths in a nine day period for this group. The mice that received the virus the last three days (subgroup 3 & 4) did not start dying until day 18 or 12 days after the first virus inoculation. Ten of the twenty animals (50%) died during the next five days. Seven additional mice died over the next six days. There were 17 deaths in an 11 day period. The animals in subgroup 3 (PBS-VIRUS) had a higher mortality during the first five days (day 18-22) than subgroup 4. During this period, 7 of the 10 deaths (70%) were from subgroup 3. The first animal in subgroup 4 did not die until day 22 while subgroup 3 had five deaths by this time. A total of 34 deaths occurred over a 19 day period starting at day 10. Twenty-nine mice (72%) developed vulvar lesions. These as a small area of erythema and swelling progressing to small vesicles followed by the area crusting.

The negative control group (Group D) received no virus or lactobacilli. This group contained a total of 15 mice with one death. This group contained three subgroups. The subgroup receiving no inoculation had a survival rate of 100%. The subgroup inoculated with only the phosphate buffered saline also had a survival rate of 100%. In these two subgroups of 0 of 10 animals died. In the subgroup receiving the micro inoculum broth and the PBS, there was carefully both externally and internally for any abnormalities. No gross abnormalities were seen. The lungs and the abdominal cavity were clear. The death of this animal gives a mortality of 20% in the MICRO-PBS group and a total negative control mortality of 7% or a survival rate of 93%.

In the post-treatment group (Group B) 9 of 20 animals died for a mortality of 45%. This group consisted of two sets of 10 animals each. In one set, 5 of 10 died (50%) and in the other set 4 of 10 died (40%). This group received viral inoculation for the first three days followed by the lactobacilli mixture for the next three days. The survival rate for this group was 55%. The first death occurred at day 10, seven days after the last virus inoculation and ten days after the first viral inoculation. On day 10 there were three deaths, two from one set (set 2) and one from the other set. It was 7 days before another death occurred (day 17). From day 17 to day 24, six animals died. There were nine deaths over a 14 day period. Of the twenty animals, seven developed small erythemic vesicles with some crusting over. All seven of these animals died.

The pre-treatment group (Group C) had a total of 3 deaths. This group consisted of two sets of ten mice each. There were two deaths in set one (20%) and one death in set two (10%). This was a total of 3 deaths out of 20 animals for a mortality of 15%. These three deaths occurred over a nine day period starting at day 13 or 7 days after the last viral inoculation. In this group the mice received the lactobacillus mixture first followed by the virus. The survival rate for this group was 85%. Four mice in this group developed lesions with three of them dying. Three of the four mice with the lesions were from set 2 with all three of these dying.

The treatment control group (Group E) consisted of ten mice and was used to test the lactobacillus preparation. This group of five mice was subdivided into two sets. One set received the lactobacilli first then the PBS. The other set received the PBS first followed by the lactobacilli. There were no deaths in this group giving a survival rate of 100%.

From this study it can be seen that a viable lactobacillus preparation has a protective effect against Herpes Simplex Virus Type 2, when topically administered to a mammal suffering from an infection of the virus.

EXAMPLE 4

A portion of the lactobacillus mixture described in Example 3, supra, was tested against cell cultures of Herpes Simplex Virus Type 2 as follows.

The cell culture studies were of two types. In one type the virus infected cells were overlayed with a nutrient agar. Filter paper discs were placed on the surface and the assay sample added. The second assay consisted of viral infected cells which were overlayed with a nutrient agar containing the assay samples. In the first series the antiviral sample was concentrated in the center and on the surface of the agar overlay. This allowed a circular diffusion of the compound out from the center. The second assay system contained the assay sample in the overlay medium and therefore gives a more uniform distribution for a more generalized response. In these tests the lactobacillus was evaluated as to its ability to prevent cell lysis due to herpes virus infection. As a control, the lactobacillus mixture was also compared to a known antiviral compound, Iododeoxyuridine (IDU). Results of these assays can be seen in Tables 4–6, below. Tables 4 and 5 give the results of the disc method. Table 4 summarizes the data obtained from cultures of human embryonic foreskin cells and Table 5 summarizes the data from human embryonic lung cells. The results shown in Table 6 are from the sample overlay method. All three procedures demonstrate a positive antiviral activity attributed to the mixture of lactobacillus. In each case the lactobacillus reduced the amount of cell lysis.

TABLE 4

THE ANTIVIRAL ACTIVITY OF IODODEOXYURIDUNE AND A LACTOBACILLUS MIXTURE AGAINST HERPES SIMPLEX VIRUS TYPE 2 IN CELL CULTURE (MRC-V)

| | DIAMETER OF MONOLAYER IN MILLIMETERS | | | | | | |
|---|---|---|---|---|---|---|---|
| | NO VIRUS NEGATIVE CONTROL | | | VIRUS: 300 PFU/PLATE POSITIVE TREATMENT | | | |
| DILUTIONS (IDU) (CON) | LAC | IDU | PBS | NO DISC | PBS | TDU | LAC |
| 1:1 (50 mcg) | 56 | 56 | 56 | 0 | 0 | 40 | 28 |
| 1:2 (25 mcg) | — | — | — | — | — | 34 | 23 |
| 1:3 (17 mcg) | — | — | — | — | — | 26 | 19 |

TABLE 4-continued

THE ANTIVIRAL ACTIVITY OF IODODEOXYURIDUNE AND A LACTOBACILLUS MIXTURE AGAINST HERPES SIMPLEX VIRUS TYPE 2 IN CELL CULTURE (MRC-V)

| DILUTIONS (IDU) (CON) | DIAMETER OF MONOLAYER IN MILLIMETERS | | | | | | |
|---|---|---|---|---|---|---|---|
| | NO VIRUS NEGATIVE CONTROL | | | VIRUS: 300 PFU/PLATE POSITIVE TREATMENT | | | |
| | LAC | IDU | PBS | NO DISC | PBS | TDU | LAC |
| 1:2 (13 mcg) | — | — | — | — | — | 22 | 18 |
| 1:1 (10 mcg) | — | — | — | — | — | 19 | 10 |

LAC: Lactobacillus Mixture
IDU: 5-Iodo-2'-Deoxyuridine
PBS: Phosphate Buffered Saline

TABLE 5

THE ANTIVIRAL ACTIVITY OF IODODEOXYURIDINE AND A LACTOBACILLUS MIXTURE AGAINST HERPES SIMPLEX VIRUS TYPE 2 IN CELL CULTURE (MRC-V)

| DILUTIONS (IDU) (CON) | DIAMETER OF MONOLAYER IN MILLIMETERS | | | | | | |
|---|---|---|---|---|---|---|---|
| | NO VIRUS NEGATIVE CONTROL | | | VIRUS: 300 PFU/PLATE POSITIVE TREATMENT | | | |
| | LAC | IDU | PBS | NO DISC | PBS | IDU | LAC |
| 1:1 (50 mcg) | 56 | 56 | 56 | 0 | 0 | 40 | 29 |
| 1:2 (25 mcg) | — | — | — | — | — | 27 | 22 |
| 1:3 (17 mcg) | — | — | — | — | — | 22 | 13 |
| 1:2 (13 mcg) | — | — | — | — | — | 20 | 09 |
| 1:1 (10 mcg) | — | — | — | — | — | 12 | 07 |

LAC: Lactobacillus Mixture
IDU: 5-Iodo-2'-Deoxyuridine
PBS: Phosphate Buffered Saline

TABLE 6

THE ANTIVIRAL ACTIVITY OF LACTOBACILLI VS IODODEOXYURIDINE IN CELL CULTURE (MRC-V) WHEN TESTED AGAINST HERPES SIMPLEX VIRUS TYPE 2 POST VIRAL INCUBATION TIME BEFORE ADDITION OF ASSAY SAMPLE

| | NO. OF PLAQUE FORMING UNITS PER PLATE TIME OF INCUBATION (HOURS) | | | | | | | |
|---|---|---|---|---|---|---|---|---|
| SAMPLE | 0 | 2 | 4 | 6 | 8 | 10 | 12 | 14 |
| IDU | 24 | 32 | 46 | 64 | 84 | 88 | 93 | 114 |
| LAC | 10 | 14 | 32 | 95 | 125 | 150 | 160 | 163 |
| EMEM | 300 | 300 | 300 | 300 | 300 | 300 | 300 | 300 |

IDU: Iododeoxyuridine
LAC: Lactobacillus Mixture
EMEM: Minimum Essential Medium, Earle's Base Although the method of the invention is preferably carried out by the topical administration of the lactobacillus culture to oral or genital sites of the afflicted mammal, topical administration is not the only mode of administration. Systemic administration, particularly by oral routes, is also possible.

The invention relates also to pharmaceutical dosage unit forms for systemic (oral) administration and topical administration, which are useful for the suppression or prevention of active herpes type 2 viral infection in mammals and alleviation of suffering from active infection. The term "dosage unit form" as used in this specification and in the claims refers to physically discrete units suitable as unitary dosages for mammalian subjects, each unit containing a predetermined quantity of the essential active ingredient, i.e., a viable colony of the above-described lactobacillus, calculated to produce the desired effect in combination with the required pharmaceutical means which adapt said ingredient for administration. Examples of dosage unit forms in accordance with this invention are preparations in liquid vehicles for oral administration and dry preparations for the extemporaneous preparation of peroral or topical preparations in a liquid vehicle.

Unit dose forms of pharmaceutical compositions useful for peroral administration contain sufficient of the active ingredient to initiate growth of the above-described mammal, in combination with a pharmaceutically acceptable carrier. For their production, the active substance is combined, for example, with solid, pulverulent carrier substances such as lactose, saccharose, sorbitol, mannitol, starches such as potato starch, maize starch or amylopectin, and furthermore laminaria powder or citrus pulp powder, cellulose derivatives or gelatine, if necessary with the addition of lubricants such as magnesium stearate or calcium stearate or polyethylene glycols, to form tablets or dragee cores. The dragee cores are coated, for example, with concentrated sugar solutions, which, for example, may furthermore contain gum arabic talcum and/or titanium dioxide, or with a lacquer which is dissolved in easily fusible organic solvents or solvent mixtures. Colorants may be added to these coatings, for example to identify different doses of active substance.

As further unit dose forms for oral administration there are suitably dry-filled capsules of gelatine and also soft, closed capsules of gelatine and a plasticizer such as glycerine. The dry-filled capsules contain the active substance, preferably in the form of a dry-lyophilized powder in admixture with fillers such as maize starch, and/or lubricants such as talcum or magnesium stearate. In soft capsules the active substance is preferably dissolved glycols, and stabilizers may also be added.

As peroral forms of use that are not in unit dose form there may be considered syrups prepared in the usual manner, for example, those which contain the active substance, preferably together with the usual adjuncts such as polysaccharide or polyalcohols, for example, sorbitol, sweeteners and/or flavoring substances.

The peroral dosage depends on the method of administration, the age and individual condition of the patient to be treated and is between about 0.01 and 5.0 mg/kg, preferably form 0.1 to 2.0 mg/kg, daily. The dosage also depends especially on the intensity of the symptoms and accordingly also on whether the infection is active or the use is prophylactic.

As unit dose forms according to the invention for vaginal use there may be considered, for example, suppositories which consist of a combination of active substance with a suppository base substance. Suitable suppository base substances are, for example, natural or synthetic triglycerides, paraffin hydrocarbons, polyethylene glycols or higher alkanols. Also suitable are gelatine rectal capsules which consist of a combination of the active substance with a base material. Suitable base substances are, for example, liquid triglycerides, polyethylene glycols or paraffin hydrocarbons.

Pharmaceutical preparations for topical use are creams, ointments, gels, vaginal-ovula, pastes, foams, tinctures and solutions, which contain from about 0.1% to 1% of the active substance.

Creams are oil-in-water emulsions, which contain more than 50% of water. As oily bases there are used principally fatty alcohols, for example, lauryl, cetyl or stearyl alcohol, fatty acids, for example, palmitic or stearic acid, liquid to solid waxes, for example, isopropyl myristate, wool wax or bees wax, and/or hydrocarbons, for example, soft paraffins (petrolatum) or paraffin oil. Emulsifiers may be surface-active substances having predominantly hydrophilic properties, such as suitable non-ionic emulsifiers, for example, fatty acid esters of polyalcohols or ethylene oxide adducts thereof, such as polyglycerine fatty acid esters or polyoxyethylene sorbitan fatty acid esters, and also polyoxyethylene fatty alcohol ethers or polyoxyethylene fatty acid esters, or corresponding ionic emulsifiers, such as alkali metal salts of fatty alcohol sulfates, for example, sodium cetyl sulfate or sodium stearyl sulfate, which are normally used in the presence of fatty alcohols, for example, cetyl alcohol or stearyl alcohol. Additives to rate at which the creams dry out, for example, poly-alcohols such as glycerine, sorbitol, propylene glycol and/or polyethylene glycols, and also preservatives, perfumes, etc.

Ointments are water-in-oil emulsions, which contain up to 70%, but preferably from about 20% to about 50% of water or aqueous phase. The fatty phase may be especially hydrocarbons, for example, soft paraffins, paraffin oil and/or hard paraffin oil and/or hard paraffins, which for improving the water-binding ability preferably contain suitable hydroxy compounds such as fatty alcohols or esters thereof, for example, cetyl alcohol or wool wax alcohols, or wool wax. Emulsifiers are corresponding lipophilic substances, such as sorbitan fatty acid esters (spans), for example, sorbitan oleate and/or sorbitan isostearate. Additives to the aqueous phase are, among others, moisture-retaining agents such as polyalcohols, for example, glycerine, propylene glycol, sorbitol and/or polyethylene glycol, and also preservatives, perfumes, etc.

Fatty ointments are water-free and contain as a base especially hydrocarbons, for example paraffin, soft paraffins and/or liquid paraffins, furthermore natural or partly synthetic fats, for example, coconut fatty acid triglyceride, or preferably hardened oils, for example hydrogenated ground nut oil or castor oil, also fatty acid partial esters of glycerine, for example, glycerine mono- or di-stearate, and also, for example, the fatty alcohols mentioned in connection with the ointments and which increase the water-absorbing capacity, and emulsifiers and/or additives.

Pastes are creams and ointments having secretion absorbing powder constituents such as metal oxides, for example titanium oxide or zinc oxide, and also talcum and/or aluminum silicates, which have the function of binding moisture or secretions present.

Gels are especially aqueous solutions of active substances in which gel formers, preferably those from the group of cellulose ethers such as, for example, methylcellulose, hydroxyethylcellulose or carboxymethylcellulose, or the vegetable hydrocolloids, such as sodium alginate, tragacanth or gum arabic, are dispersed and swollen up. Furthermore, the gels contain preferably also moisture-retaining agents of the group of polyalcohols, such as propylene glycol, glycerine and/or lower polyethylene glycols, and also wetting agents, for example polyoxyethylene sorbitan fatty acid esters, such as polyoxyethylene sorbitan monolaurate. As further added substances the gels may contain the usual preservatives, for example, benzyl alcohol, phenethyl alcohol, phenoxyethanol, p-hydroxybenzoic acid lower alkyl esters such as the methyl and/or propyl ester, sorbic acid or alkali metal salts thereof, or organic mercury compounds such as merthiolate.

Tinctures and solutions generally have an aqueous-ethanolic or aqueous base, which contains, inter alia, polyalcohols such as, for example, propylene glycol or glycerine and/or lower polyethylene glycols, as moisture-retaining agents for reducing evaporation, and if necessary re-fatting substances such as fatty acid esters of lower polyethylene glycols, that is to say, lipophilic substances soluble in the aqueous-ethanolic mixture, as substitutes for the fatty substances withdrawn from the skin by the ethanol, and if desired further adjuncts and additives, besides the usual preservatives such as those mentioned above and, for example, also the previously mentioned polyoxyethylene sorbitan fatty acid esters such as polyoxyethylene sorbitan monolaurate.

The manufacture of the pharmaceutical preparations for topical use is carried out in a manner known per se, for example, by dissolving or suspending the active substance in the base or, if necessary, at first in a part thereof. In working up the active substance as a solution it is generally dissolved in one of the two phases before emulsification, in working up in the form of a suspension the solid, preferably finely ground active substance, after being dispersed, is mixed with a part of the base and then added to the remainder of the base.

The preparations of the invention may contain, in addition to the usual preservatives, further biologically active, for example, antiphlogistically or antimicrobially active, such as antibacterially, antifungally or also antivirally active substances, for example, Flumethasone, Neomycin, Gentamycin, lactic acid or Miconazole, provided they do not affect the growth of the viable culture.

The topical preparations of the invention are suitable especially for the treatment of Herpes genitalis, Herpes dermatitis and Herpes labialis. For example, for the treatment of the first two, gels or ointments of the invention are applied, for example, by means of a tube or applicator 2 to 3 times daily, and for the treatment of Herpes labialis several times daily, to the affected parts of the body until the symptoms recede or until healing occurs. Aqueous solutions of the invention may be used, for example, for washing affected body cavities, especially for the treatment of Herpes gingivostomatitis or for the treatment of Herpes keratoconjunctivitis.

What is claimed:

1. A method of alleviating the suffering of a mammal suffering from the active phase of a herpes simplex virus infection, which comprises; applying topically to the infected areas of the mammal, an effective amount for alleviating suffering of a viable bacterial culture selected from the group consisting of *Lactobacillus acidophilus*, *Lactobacillus bulgaricus* and mixtures thereof.

2. The method of claim 1 wherein the virus is type 2 and the infected area is the genital area.

3. The method of claim 2 wherein the mammal is a female and application is with a catamenial tampon.

4. The method of claim 2 wherein the mammal is a male and application is with a moistened penis sheath.

* * * * *